United States Patent
Mou et al.

(10) Patent No.: US 12,274,755 B2
(45) Date of Patent: Apr. 15, 2025

(54) SILICA NANOSPHERE FOR IMMUNOTHERAPY

(71) Applicant: NANO TARGETING & THERAPY BIOPHARMA INC., Taipei (TW)

(72) Inventors: Chung-Yuan Mou, Taipei (TW); Cheng-Hsun Wu, Zhubei (TW); Si-Han Wu, Taoyuan (TW); Yi-Ping Chen, Keelung (TW)

(73) Assignee: NANO TARGETING & THERAPY BIOPHARMA INC., Taipei (TW)

( * ) Notice: Subject to any disclaimer, the term of this patent is extended or adjusted under 35 U.S.C. 154(b) by 0 days.

(21) Appl. No.: 16/932,380

(22) Filed: Jul. 17, 2020

(65) Prior Publication Data

US 2021/0015943 A1 Jan. 21, 2021

Related U.S. Application Data

(60) Provisional application No. 62/875,842, filed on Jul. 18, 2019.

(51) Int. Cl.
| | | |
|---|---|---|
| A61K 47/69 | (2017.01) | |
| A61K 9/51 | (2006.01) | |
| A61K 39/00 | (2006.01) | |
| A61P 35/00 | (2006.01) | |
| B82Y 5/00 | (2011.01) | |

(52) U.S. Cl.
CPC ........ A61K 47/6923 (2017.08); A61K 9/5115 (2013.01); A61K 39/0011 (2013.01); A61K 39/001106 (2018.08); A61P 35/00 (2018.01); B82Y 5/00 (2013.01)

(58) Field of Classification Search
CPC ......... A61K 9/14; A61K 31/695; A61K 47/07
See application file for complete search history.

(56) References Cited

U.S. PATENT DOCUMENTS

| | | | |
|---|---|---|---|
| 2011/0229576 A1* | 9/2011 | Trogler | A61K 9/14 424/193.1 |
| 2016/0038608 A1 | 2/2016 | Mou et al. | |
| 2018/0050115 A1* | 2/2018 | Mou | A61P 37/04 |

FOREIGN PATENT DOCUMENTS

| | | |
|---|---|---|
| CN | 107753464 A | 3/2018 |
| TW | I611812 B | 1/2018 |

OTHER PUBLICATIONS

Miao Kong et al. Biodegradable Hollow Mesoporous Silica Nanoparticles for Regulating Tumor Microenvironment and Enhancing Antitumor Efficiency, Theranostics, 7(13), 3276-3292. (Year: 2017).*
Ziwei Deng et al. Hollow chitosan-silica nanospheres as pH-sensitive targeted delivery carries in breast cancer therapy, Biomaterials, 32, 4976-5986. (Year: 2011).*
Yuchen Fan et al. Nanoparticle drug delivery system designed to improve cancer vaccines and immunotherapy, Vaccines, 3, 662-685. (Year: 2017).*
Juanjuan Peng et al., Hollow silica nanoparticles loaded with hydrophobic phthalocyanine for near-infrared photodynamic and photothermal combination therapy, Biomaterials, 34, 7905-7912. (Year: 2013).*
Zhenfu Wen et al., Recent development in biodegradable nanovehicle delivery system-assisted immunotherapy, Biomater. Sci , 7, 4414-4443. (Year: 2019).*
Shan Gao et al., Engineering Nanoparticles for Targeted Remodeling of the Tumor Microenvironment to Improve Cancer Immunotherapy, Theranostics, 9, 126-151. (Year: 2019).*
Peng, Juanjuan, et al. "Hollow silica nanoparticles loaded with hydrophobic phthalocyanine for near-infrared photodynamic and photothermal combination therapy." Biomaterials 34.32 (2013): 7905-7912.
An, Lu, et al. "Paramagnetic hollow silica nanospheres for in vivo targeted ultrasound and magnetic resonance imaging." Biomaterials 35.20 (2014): 5381-5392.
Extended European Search Report in EP Application No. 20186407.1 dated Dec. 15, 2020, in 6 pages.
Wang, Xiupeng, et al. "Stimulation of in vivo antitumor immunity with hollow mesoporous silica nanospheres." Angewandte Chemie 128.5 (2016): 1931-1935.
Dellacherie, Maxence O., et al. "Covalent conjugation of peptide antigen to mesoporous silica rods to enhance cellular responses." Bioconjugate Chemistry 29.3 (2018): 733-741.
Search Report in Office Action from TW Appln. 109124259, dated Sep. 13, 2021, in 11 pages.
Office Action issued Mar. 13, 2024 by the China National Intellectual Property Administration (CNIPA) in counterpart CN Appln.: 202010693282.3.
Maxence O. Dellacherie et al.: "Covalent Conjugation of Peptide Antigen to Mesoporous Silica Rods to Enhance Cellular Responses", Bioconjugate Chem,, vol. 29, pp. 733-741, Pub. Date: Jan. 10, 2018.
China Second Office Action for Application No. 202010693282.3, mailed on Sep. 29, 2024, 12 pages.
Wilbowo, David et al., "Emulsion-templated silica nanocapsules formed using bio-inspired silicification," Chem. Commun., 2014, 50, 11325, Aug. 7, 2014, 4 pages.
Malmsten, Martin, "Inorganic nanomaterials as delivery systems for proteins, peptides, DNA, and siRNA," Current Opinion in Colloid & Interface Science 18 (2013) 468-480, 13 pages.

* cited by examiner

*Primary Examiner* — Michael G. Hartley
*Assistant Examiner* — Jagadishwar R Samala
(74) *Attorney, Agent, or Firm* — LADAS & PARRY LLP

(57) ABSTRACT

The present disclosure relates to a field of hollow silica nanospheres. Particularly, the present disclosure relates to silica nanoparticles as adjuvant to induce or enhance immune response or as carrier to deliver antigen to a body.

14 Claims, 8 Drawing Sheets

SILICA NANOSPHERE FOR IMMUNOTHERAPY

FILED OF THE INVENTION

The present disclosure relates to a field of hollow silica nanospheres. Particularly, the present disclosure relates to silica nanoparticles as adjuvant to induce or enhance immune response or as carrier to deliver antigen to a body.

BACKGROUND OF THE INVENTION

Mesoporous silica nanoparticles are deemed to have great potential as drug delivery systems due to their chemical/thermal stability, large surface area, high loading capacity, adjustable surface properties and excellent biocompatibility. Among various silica nanomaterials, the morphology and characteristics of hollow silica nanospheres (HSNs) are different from common mesoporous silica nanoparticles in having a hollow interior space and thin porous shell which enable them to encapsulate macromolecules (such as bioactive ingredients) and exhibit higher loading capacity due to the large internal space; such purposes can be achieved, for example, by adjusting the pore size of the shell. When the pore size is smaller than the macromolecules, the shell can keep the macromolecules from leaking out during circulation in blood. The morphology and characteristics of HSNs greatly depend on the synthetic strategies, which differ from applications to applications. This invention explores the potential of HSNs acting as carrier and adjuvant to enhance the efficacy of medical applications, e.g., vaccination.

SUMMARY OF THE INVENTION

The inventors surprisingly found that HSNs per se can induce immune response in a subject and thus can be used as an antigen/adjuvant in immunotherapy. Furthermore, HSNs can also be used as carrier carrying antigen(s) (such as neoantigen) in immunotherapy.

Accordingly, the present disclosure relates to HSNs enclosing a small bioactive ingredient therein and applications thereof in therapy, in particular immunotherapy. In particular, the small bioactive ingredient is a neoantigen such as tumor-specific neoantigen, peptide, a DNA, an RNA, etc.

Hence, the present disclosure provides a method for inhibiting tumor growth in a subject in need thereof, comprising administration of hollow silica nanospheres (HSNs) to the subject thereby increasing tumor-infiltrating immune cells in tumor, wherein the HSNs comprises a single or multi-layered silica shells, wherein each shell has meso-pores and encloses an closed hollow space, optionally the innermost hollow closed space has a solid silica core, wherein the space is defined by the distance between any two silica shells or the solid silica core, and wherein the hydrodynamic size of HSNs in a medium measured via Dynamics Light Scattering (DLS) is no greater than 150 nm, wherein the medium is biologically similar to or equivalent to phosphate buffered saline (PBS). In one embodiment, the tumor-infiltrating immune cells include, but are not limited to, T cells, B cells, natural killer cells, macrophages, neutrophils, dendritic cells, mast cells, eosinophils, basophils, etc.

The present disclosure also provides a method for inducing an immune response in a subject in need thereof, comprising administration of hollow silica nanospheres (HSNs) to the subject, wherein the HSNs comprises a single or multi-layered silica shells, wherein each shell has meso-pores and encloses an closed hollow space, optionally the innermost hollow closed space has a solid silica core, wherein the space is defined by the distance between any two silica shells or the solid silica core, and wherein the hydrodynamic size of HSNs in a medium measured via Dynamics Light Scattering (DLS) is no greater than 200 nm, wherein the medium is biologically similar to or equivalent to phosphate buffered saline (PBS).

The present invention also provides a hollow silica nanosphere (HSN) conjugate comprising a HSN and a small bioactive ingredient enclosed in the HSN, wherein the HSNs comprises a single or multi-layered silica shells, wherein each shell has meso-pores and encloses an closed hollow space, optionally the innermost hollow closed space has a solid silica core, wherein the space is defined by the distance between any two silica shells or the solid silica core, and wherein the hydrodynamic size of HSN in a medium measured via Dynamics Light Scattering (DLS) is no greater than 200 nm, wherein the medium is biologically similar to or equivalent to phosphate buffered saline (PBS).

DETAIL DESCRIPTION OF THE INVENTION

Figure 1:
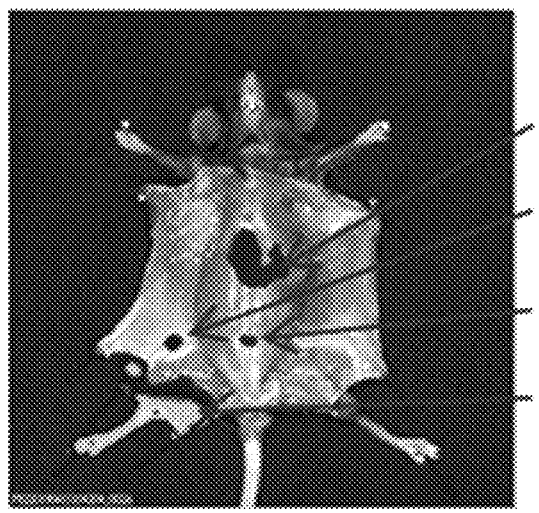
FIG. 1 shows show the 50 nm HSN with ability of targeting lymph node.
Figure 1:
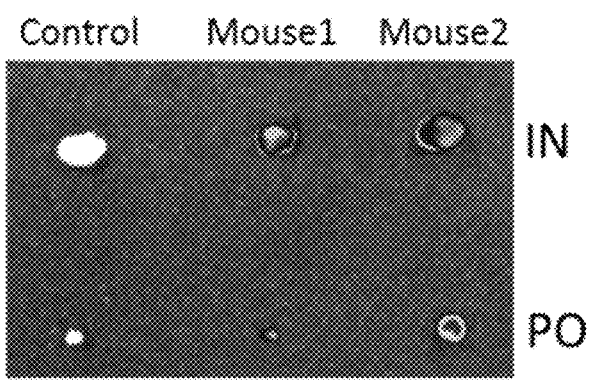

In order to facilitate the understanding of the disclosure herein, terms as used herein are hereby defined below.

In the context of the specification and the claims, the singular forms "a", "an" and "the" include plural referents, unless specifically indicated otherwise. Unless otherwise stated, any and all examples or exemplary language (e.g., "such as") provided herein are merely used for better illustration of the present invention, instead of limiting the scope of the present invention.

It is to be understood that any numerical range recited in this specification is intended to include all sub-ranges encompassed therein. For example, a range from "50 to 70° C." includes all sub-ranges and specific values between the stated minimum value of 50° C. and the stated maximum value of 70° C., inclusive, e.g. from 58° C. to 67° C., and from 53° C. to 62° C., 60° C. or 68° C. Since the numerical ranges disclosed are continuous, they contain each numerical value between the minimum and maximum value. Unless otherwise specified, the various numerical ranges indicated in this specification are approximate.

In the present invention, the term "about" refers to an acceptable deviation of a given value measured by a person of ordinary skill in the art, depending, in part, on how to measure or determine the value.

In the present invention, unless particularly specified, the prefix "nano-" as used herein means a size of about 300 nm or less. Unless particularly specified, the prefix "meso-" as used herein, unlike the definition suggested by IUPAC, means a size of about 5 nm or less.

In the present invention, the term "silane" as used herein refers to derivatives of SiH4. Normally, at least one of the four hydrogens is replaced with substituents such as alkyl, alkoxyl, amino, etc. as described below. The term "alkoxysilane" as used herein refers to a silane having at least one alkoxyl substituent directly bonded to the silicon atom. The term "organo-alkoxysilane" as used herein refers to a silane having at least one alkoxyl substituent and at least one hydrocarbyl substituent directly bonded to the silicon atom. The term "silicate source" as used herein refers to substances which can be deemed as a salt form or an ester form of orthosilicic acid, for example sodium orthosilicate, sodium metasilicate, tetraethyl orthosilicate (tetraethoxysilane, TEOS), tetramethylorthosilicate, tetrapropylorthosilicate. Optionally, the hydrocarbyl substituent can be further substituted or interrupted with a heteroatom.

In the present invention, the term "hydrocarbyl" as used herein refers to a mono-valent radical derived from hydrocarbons. The term "hydrocarbon" as used herein refers to a molecule that consists of carbon and hydrogen atoms only. Examples of the hydrocarbons include, but are not limited to, (cyclo)alkanes, (cyclo)alkenes, alkadienes, aromatics, etc. When the hydrocarbyl is further substituted as mentioned above, the substituent can be halogens, amino groups, a hydroxy group, a thiol group, etc. When the hydrocarbyl is interrupted with a heteroatom as mentioned above, the heteroatom can be S, O or N. In the present invention, a hydrocarbyl preferably comprises 1 to 30 C atoms.

In the present invention, the term "alkyl" refers to a saturated, straight or branched alkyl, which comprises preferably 1-30 carbon atoms, and more preferably 1-20 carbon atoms. Examples of alkyl include, but are not limited to, methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl or the like.

In the present invention, the term "alkoxyl" or "alkoxy" as used herein means a group having a formula "—O-alkyl," wherein the definition of the "alkyl" in said formula has the meaning of "alkyl" as stated above.

In the present invention, the term "cycloalkyl" as used herein means a saturated or partially unsaturated cyclic carbon radical containing 3 to 10 ring carbon atoms and more preferably 3 to 8 ring carbon atoms, and optionally an alkyl substituent(s) on the ring. Examples of cycloalkyl include, but are not limited to, cyclopropyl, cyclopropenyl, cyclobutyl, cyclopentyl, cyclohexyl, 2-cyclohexen-1-yl, and the like.

In the present invention, the term "halogen" or "halo" denotes fluorine, chlorine, bromine or iodine.

In the present invention, the term "amino" as used herein means a functional group of the formula —NR1R2, wherein R1 and R2 each independently represent hydrogen or a hydrocarbyl group as defined above.

In the present invention, the term "aqueous phase" as used herein means a phase substantively miscible with water. Examples of the aqueous phase include, but are not limited to, water per se, aqueous buffers, aqueous dimethylsulfoxide (DMSO) solutions, aqueous alkanolic solutions, etc. The aqueous phase may be adjusted to be acidic, neutral or alkaline, based on the demand of the synthesis and/or the stability of the substance present in the aqueous phase.

In the present invention, the term "oil phase" as used herein means a phase substantively immiscible with the aqueous phase as mentioned above. Examples of the oil phase include, but are not limited to, liquid, substituted or unsubstituted (cyclo)alkanes, such as hexane, decane, octane, dodecane, cyclohexane, etc.; substituted or unsubstituted aromatic solvents, such as benzene, toluene, xylene, etc.

In the present invention, the term "bioactive ingredient" as used herein refers to substance having an activity in an organism. Examples of the bioactive ingredient include, but are not limited to, an enzyme, a protein drug, an antibody, a vaccine, an antigen, an antibiotic or a nucleotide drug.

In the present invention, the term "neoantigen" as used herein refers to a bioactive ingredient having a smaller size, such as a peptide, a DNA, an RNA, a nucleotide, etc.

Medical Applications of Hollow Silica Nanospheres (HSNs)

The inventors surprisingly found that, in addition to acting as drug deliverers, hollow silica nanospheres (HSNs) per se may exhibit certain characteristics useful in medical applications, in particular immunotherapy.

In one aspect, the present disclosure provides a method for inhibiting tumor growth in a subject in need thereof, comprising administration of hollow silica nanospheres (HSNs) to the subject thereby increasing tumor-infiltrating immune cells in tumor, wherein the HSNs comprises a single or multi-layered silica shells, wherein each shell has meso-pores and encloses an closed hollow space, optionally the innermost hollow closed space has a solid silica core, wherein the space is defined by the distance between any two silica shells or the solid silica core, and wherein the hydrodynamic size of HSNs in a medium measured via Dynamics Light Scattering (DLS) is no greater than 150 nm, wherein the medium is biologically similar to or equivalent to phosphate buffered saline (PBS). In one embodiment, the tumor-infiltrating immune cells include, but are not limited to, T cells, B cells, natural killer cells, macrophages, neutrophils, dendritic cells, mast cells, eosinophils, basophils, etc.

In some embodiments, the size of the HSNs ranges from 30 to 150 nm, preferably from 40 to 100 nm.

It should be noted that the size, e.g., hydrodynamic size, etc., of HSNs may be critical for determining whether they are suitable for applications. Transmission electron microscopy (TEM) is one conventional means for measuring the "original" size of nanoparticles, while the hydrodynamic size may more closely reflect the "apparent" size of the nanoparticles present in a medium. In particular, the hydrodynamic size of HSNs may directly determine whether they can be applied in living subjects. If the hydrodynamic size of HSNs is too large, they would be easily aggregate or grow in media. This phenomenon, i.e. aggregation, not only hampers the delivery efficient but may also result in negative effects in medical applications, e.g., clogging in circulatory system, rapid clearance by immune system, etc. The hydrodynamic size can be measured by Dynamics Light Scattering (DLS)

In another aspect, a method for inducing an immune response in a subject in need thereof, comprising administration of hollow silica nanospheres (HSNs) to the subject, wherein the HSNs comprises a single or multi-layered silica shells, wherein each shell has meso-pores and encloses an closed hollow space, optionally the innermost hollow closed space has a solid silica core, wherein the space is defined by the distance between any two silica shells or the solid silica core, and wherein the hydrodynamic size of HSNs in a medium measured via DLS is no greater than 200 nm, wherein the medium is biologically similar to or equivalent to phosphate buffered saline (PBS).

In one embodiment, the HSNs and process of preparing the same described in U.S. Ser. No. 15/681,207 may be applicable in the present invention, which is incorporated herein by reference in its entirety.

Small Bioactive Ingredients/Neoantigens Enclosed in HSNs

The present invention also provides a hollow silica nanosphere (HSN) conjugate comprising a HSN and a small bioactive ingredient enclosed in the HSN, wherein the HSNs comprises a single or multi-layered silica shells, wherein each shell has meso-pores and encloses an closed hollow space, optionally the innermost hollow closed space has a solid silica core, wherein the space is defined by the distance between any two silica shells or the solid silica core, and wherein the hydrodynamic size of HSN in a medium measured via Dynamics Light Scattering (DLS) is no greater than 200 nm, wherein the medium is biologically similar to or equivalent to phosphate buffered saline (PBS).

Without being bound to the theory, when the HSNs have a size (e.g., measured by TEM) of no greater than 100 nm and a hydrodynamic size (e.g., measured by DLS) of no greater than 200 nm, in particular no greater than 150 nm, they exhibit excellent dispersity and characteristics of targeting lymph nodes and tumor. Given this, HSNs are suitable for carrying bioactive ingredients, such as antigen, neoantigen, etc. In particular, the bioactive ingredients are enclosed within the pores such that they will not leak out during the delivery in the subject. This ensures the bioactive ingredients not to be degraded by protease existing in the subject and to arrive at the same position where immune cells exist, thereby enhancing immune response. The structure also allows bioactive ingredients be in a higher level per unit volume of the HSNs.

The pore size of shell of HSNs can be adjusted; when the pore size is smaller than the size of the bioactive ingredient, e.g., macromolecules, the shell can keep the bioactive ingredient, e.g., macromolecules, from leaking out during their circulation in blood. The morphology and characteristics of HSNs greatly depend on the synthetic strategies, which differ from applications to applications. The inventors thus make applications based on the effects that HSNs can be applied as a carrier and adjuvant, thereby enhancing the efficacy of vaccination, etc.

The inventors also surprisingly found that, when using microemulsion process to produce HSNs enclosing certain bioactive ingredients, such as peptides, the level of bioactive ingredients loaded by the HSNs might be insufficient or lower than other types of bioactive ingredients. Without being bound to the theory, the cause may be forming reverse microemulsion during the process since peptide may have affinity toward the surfactant used in the microemulsion process of forming HSNs. To solve this problem, the inventors found that the bioactive ingredient can be modified to create difference between affinities of the bioactive ingredient to the surfactant and to the silica, i.e., more tendency toward the silica, such that the bioactive ingredient could be more easily enclosed by the HSNs. The other approach is to introduce molecules having high affinity toward the bioactive ingredients.

Hence, in some embodiments, the small bioactive ingredient is modified to have a structure of $Y_{(n)}$-X-SBI-$[X-Y_{(m)}]_{(r)}$, wherein Y is a peptide with positive charge, X is a enzyme-cleavable sequence, SBI is a small bioactive ingredient and each of n, m and r is an integer, wherein at least one of n and m×r is not zero. In one embodiment, n is an integer other than zero and r is 0. In one embodiment, each of m and r is an integer other than zero and n is 0. In one embodiment, each of n, m and r is an integer other than zero.

In some embodiments, the small bioactive ingredient is modified to have a structure of $Y_{(n)}$-$X_{(a)}$-SBI-$X_{(b)}$-$Y_{(m)}$, wherein Y is a peptide with positive charge, X is a enzyme-cleavable sequence, SBI is a small bioactive ingredient and each of b, n, m and r is an integer, wherein at least one of n and m is not zero. In one embodiment, each of b and m is an integer other than zero and n and a are 0. In one embodiment, each of n and a is an integer other than zero and b and m are 0. In one embodiment, each of b, n, m and r is an integer other than zero.

In some embodiments, the bioactive ingredient is modified to have a structure of $Z_{(c)}$-$Y_{(n)}$-$X_{(a)}$-SBI-$X_{(b)}$-$Y_{(m)}$-$Z_{(d)}$, wherein Z is a thiol group containing molecule, Y is a peptide with positive charge, X is a enzyme-cleavable sequence, SBI is a small bioactive ingredient and each of a, b, c, d, m and n is an integer, wherein at least one of c, d, m and n is not zero. In one embodiment, each of b, m and d is an integer other than zero and n, a and c are 0. In one embodiment, each of b and m is an integer other than zero and n, a, c and d are 0. In one embodiment, each of b and d is an integer other than zero and n, a, c and m are 0. In one embodiment, each of n, a and c is an integer other than zero and b, m and d are 0. In one embodiment, each of n and a is an integer other than zero and b, m, d and c are 0. In one embodiment, each of c and a is an integer other than zero and b, m, d and n are 0.

In such cases, Y and Z could provide affinity toward HSNs, which normally bear slightly negative charge on the surface X, the enzyme-cleavable sequence, may be cleaved by enzyme, such as protease, present in the subject to which the HSNs are administered, such that the SBI can be released to the environment. Details of these groups are also described elsewhere in the subject disclosure.

In some embodiments, the small bioactive ingredient is a neoantigen. Neoantigens are newly formed antigens that have not been previously recognized by the immune system. A new approach in immunotherapy that involves vaccines based on peptide neoantigens promises to bring therapeutic precision to the level of individual tumors in individual patients. Neoantigens can arise from altered tumor proteins formed as a result of tumor mutations or from viral proteins. Examples of the neoantigen include, but are not limited to, a tumor-specific neoantigen, a tumor neo-epitope, a neoantigenic peptide, a neoantigenic DNA, and a neoantigenic RNA.

In some embodiments, the small bioactive ingredient is an antigen derived from virus, bacteria, or microorganism.

Peptides that comprise know tumor specific mutations, and mutant polypeptides or fragments of tumor-epitope. These peptides and polypeptides are referred to herein as "neoantigenic peptides" or "neoantigenic polypeptides".

Recently, silica nanoparticles have been reported as potential immunoadjuvants in vaccines. A vaccine typically contains two principal components: antigen and adjuvants. The antigen can be derived from the fragment of disease-causing organisms or surface protein of cancer cell recognized by an antigen-specific receptor. However, most antigens used for vaccine typically suffer from poor immunogenicity, weak immune response, and poor immune memory when the antigen is used alone. Adjuvants are substances that induce, potentiate, accelerate, and prolong the specific immune response against the antigen. For a vaccine, adjuvants play a key role in generating a robust and long-lasting adaptive immune response against an antigen. Moreover, an ideal adjuvant should act as both an antigen delivery vehicle and an immune potentiator, because the antigen and adjuvants in a single particle should facilitate uptake by the same antigen-presenting cells (APCs) and lead to a more potent immune response.

The advantages of using silica nanoparticle as an adjuvant and carrier for vaccination include: (1) protecting antigens from degradation and denaturation; (2) efficiently targeting and activating the antigen-presenting cells; (3) increasing the concentration of antigenic molecules per volume; (4) regulating the antigen presentation pathway. Silica nanoparticles show intrinsic adjuvant activity and can effectively enhance both cellular and humoral immunity. The physiochemical properties of silica nanoparticles affect the interaction between particle and immune system. Therefore different kinds of silica nanoparticle will induce different immune responses. Silica nanoparticles for enhancing immunogenicity or immunotherapy efficacy must do two crucial jobs: (1) efficiently deliver antigens to the APCs or lymph node and (2) subsequently release antigens inside or nearby APCs and activate immune response. Silica nanoparticles can facilitate APC uptake and lymph node targeting through particle size and surface functional group modifications. Positively charged or neutrally charged nanoparticles could be uptaken by dendritic cells (DC) more effectively than negatively charged ones. Nanoparticle traffic to lymph node transpires in a size dependent manner. When large particles (>200 nm) are administrated through subcutaneous injection, the particles traffic to lymph node dependent on cellular transport by DC immigrating from the skin, but this pathway is believed to be less efficient. In contrast, small particles (<200 nm) are able to directly drain to the lymph node and be uptaken by lymph node-resident cells. Thus, small particles have the potential of lymph node targeting ability and higher antigen delivery efficiency. For improving the activation of antigen-specific immune response, the antigen delivered by nanoparticles should be protected from protease and keep intact until APC uptake. Furthermore, when the antigen is adsorbed, encapsulated or incorporated into a nanoparticle, it creates higher localized antigen concentration and leads to driving stronger immune responses than free antigens. The common way that a nanoparticle binds an antigen is by attaching the antigen on the particle surface or inner surface of pores in the particle though covalent or non-covalent bonds such as hydrophobic/hydrophilic interaction, van der Waals force, electrostatic interaction, or hydrogen bonds. However, the antigen attached on the particle surface may cause particle aggregation in stock solution or physiological solution, making it hard to produce a stable suspension solution for application. The antigen attached on a particle through a non-covalent bond may leak upon injection into the body; the leaked antigen will be degraded and the number of effective antigens delivered to APCs will be diminished. Conjugating an antigen with a particle through a covalent bond can solve the antigen leakage problem. However, the antigen cannot be released when the antigen-particle is uptaken by APCs; the particle will interfere with the interaction between antigen and antigen receptor of APCs and decrease the possibility of inducing immune response. By taking advantage of silica nanoparticles ability to serve both as antigen carrier and adjuvant, silica nanoparticles have potential to solve problems in traditional vaccine development: poor immunogenicity, weak immune response, and poor immune memory. Hence, this invention provides a method to overcome the problems mentioned above and develop (hollow) silica nanospheres which have monodisperse particle size, and provide antigen protection and good immunogenicity and immunotherapy efficacy for vaccine applications.

As noted above, the neoantigen may not be properly or efficiently encapsulated by the HSNs. The neoantigen may be a peptide, a DNA, an RNA, etc. Peptides having no more than 200 amino acids, preferably no more than 100 amino acids and more preferably no more than 50 amino acids in their sequence may be considered as neoantigen. A DNA or RNA sequence having no more than 1200 nucleobases, preferably no more than 600 nucleobases and more preferably no more than 300 nucleobases may be considered as neoantigen.

Applications of Small Bioactive Ingredient(s) Enclosed in HSNs

Therefore, in another aspect, the present disclosure provides a vaccine composition comprising the HSN conjugate of the present disclosure.

In another aspect, the present disclosure provides a method of delivering a small bioactive ingredient to a subject, comprising administrating an HSN conjugate of the present disclosure to a subject.

In another aspect, the present disclosure provides a method of delivering a neoantigen to a subject in immunotherapy, comprising administrating HSNs enclosing a neoantigen therein to a subject.

Preparation of HSNs Enclosing Small Bioactive Ingredient(s)

The present invention also provides a method of producing a hollow silica nanoparticle containing a bioactive ingredient therein:
   (a) providing a composition comprising an oil phase, a surfactant, an alkoxysilane and/or silicate source, an aqueous phase containing one or more bioactive ingredients and optionally a co-surfactant,
   (b) forming a water-in-oil (W/O) microemulsion from the composition described in step (a);
   (c) adding an initiating reagent to the W/O microemulsion of (b) to form HSNs encapsulating the bioactive ingredient(s);
   (d) performing a destabilizing condition to destabilize the W/O microemulsion and collecting the resulting particle thus formed from the microemulsion; and
   (e) dispersing the particle collected in step (d) in an aqueous washing phase to obtain the silica nanoparticle.

In a further aspect, the method comprises at least one of the following features:
   (i) the surfactant is ionic; or the surfactant is non-ionic and absent of oxyalkylene units;
   (ii) the bioactive ingredient(s) is/are modified with an amino acid sequence before used, wherein the amino acids in the sequence are those can be positively charged or contain thiol group; and
   (iii) a substance having affinity toward the bioactive ingredient(s) is/are introduced into the aqueous phase in step (a).

The surfactants used for forming a W/O microemulsion are commonly used and readily known in the art. Preferably, ionic surfactants and non-ionic surfactants which do not have oxyethylene unit(s) are used in the present invention. Examples of non-ionic surfactant which do not have oxyalkylene unit(s) include, but are not limited to, glucoside alkyl ether, glycerol alkyl ester, cocamide monoethanolamine (cocamide MEA), cocamide diethanolamine (cocamide DEA), lauryldimethylamine oxide, etc.

As noted above, the inventors found that the bioactive ingredient can be modified such that the bioactive ingredient could be more easily enclosed by the HSNs, and/or molecules having high affinity toward the bioactive ingredients can be introduced into the aqueous phase during the microemulsion process for producing HSNs.

In one embodiment, the small bioactive ingredient is modified with an amino acid sequence. In particular, the amino acids in the sequence are those can be positively charged. Examples of the amino acids which can be positively charged include, but are not limited to, arginine (R), lysine (K), histidine (H), non-natural amino acid with position(s) which can be positively charged, etc.

In one embodiment, the amino acid sequence links with the small bioactive ingredient via a linker. The linker is preferably enzyme-cleavable, such as an enzyme-cleavable amino sequence or an enzyme-cleavable nucleotide sequence.

In on embodiment, the small bioactive ingredient is modified with a thiol group containing molecule.

Examples of substances, molecules, or particles having high affinity toward the bioactive ingredients to be introduced into aqueous phase during microemulsion process include, but are not limited to, substances, molecules or particles having disulfide bond, e.g., orthopyridyl disulfide (OPSS) group, for example OPSS-PEG-NHS, 3-(2-pyridyldithio)propionyl hydrazide, Sulfo-LC-SPDP (sulfosuccinimidyl 6-(3'-(2-pyridyldithio)propionamido)hexanoate), substances, molecules or particles having thiolcholoride group, arenesulfenamide group, thiouronium salt or thiol group.

EXAMPLES

The following examples are provided to make the present invention more comprehensible to those of ordinary skill in the art to which the present invention pertains, but are not intended to limit the scope of the invention.

Materials, Methodologies and Test Models
Transmission Electron Microscopy (TEM)

Transmission electron microscopy (TEM) was used to directly examine and verify the appearance of the silica nanoparticles. The TEM images were taken on a Hitachi H-7100 transmission electron microscope operated at an accelerated voltage of 75-100 kV. Samples dispersed in ethanol or water were dropped on carbon-coated copper grids and dried in air for TEM observation.

Dynamic Light Scattering (DLS)

Size measurements of the silica nanoparticles in different solution environments were performed with Dynamic Light Scattering (DLS) on a Malvern Zetasizer Nano ZS (Malvern, UK). The (solvated) particle sizes formed in different solutions were analyzed: $H_2O$, Dulbecco's Modified Eagle Medium (DMEM) with 10% FBS, PBS buffer solution (pH7.4) and 5% Glucose at room temperature.

OPSS-Silica Nanoparticle

Synthesis process: At first step, 85.2 µL APTMS+253.2 µL OPSS-linker (50 mg OPSS-PEG-NHS, 200/mL in DMSO) mixed together, then stir at 37° C. overnight. In order to isolate APTMS-Linker-OPSS, ProElut™ C18 tube was rinsed with 3-5 mL of methanol and follow by 3-5 mL of Deionized water. The mixture was diluted from 100% DMSO to 10% DMSO solution. Load APTMS/APTMS-Linker-OPSS mixture to the top of the tube and then wash with 1 mL of 10% ACN to remove free APTMS reagent. Use 1.5 mL Methanol to elute the sample to get APTMS-Linker-OPSS. Final, concentrated the APTMS-linker-OPSS solution with rotary evaporation and quantified the stock solution by HPLC. 20 mL Decane, 3.5 mL Igepal CO-520, and 1.1 mL hexanol were mixed together and follow by 1.2 mL DI water. Stir the mixture at 20° C. for 20 minutes to be a reverse microemulsion system. Introduce 50 uL diluted APTMS (8× diluted with DI water) and 200 uL TEOS and then stir for 20 minutes. After that, add 500 uL 28% NH4OH into the system. The solution mixed at 20° C. for 11 minutes and then added 65 uL diluted APTMS (8× diluted with DI water) and 260 uL TEOS and then stirred overnight at 20° C. For modifying APTMS-linker-OPSS on the particle surface, add 15 uL TEOS and ATMPS-linker-OPSS (4.2 mg) into the system and keep the system stir for overnight. 10 mL ethanol was introduced into the solution for destroying the microemulsion system and then centrifuge for 15 min at 14000 rpm to get the OPSS-silica nanoparticle. Washed the pellet twice with ethanol and then centrifuged to remove the wash solvent. Used 80 mL DI-water to wash the OPSS-silica nanoparticle for 1 hours at 50° C. to remove residual reagent and make the particle become hollow. Wash the pellet twice with water and then centrifugal to remove the wash solvent. After the above the synthesis process, the OPSS-silica nanoparticle were obtained.

Quantification of Protein in HSN

The protein amount in HSN was quantified by two methods: (1) enzyme activity or (2) fluorescence correlation spectroscopy.

Protein@HSN quantification by enzyme activity method: if the protein encapsulated in HSN is an enzyme, the amount of protein in the HSN can be derived from the enzyme activity of protein@HSN.

ASNase@HSN quantification: ASNase activity was determined by Nessler's reagent, which was purchased from Merck. First, 100 µL of 0.05M Tris-HCl (pH=8.6) and 850 µL 0.02M L-asparagine were mixed, 50 µL of 1.5M trichloroacetic acid (TCA) was added for a blank, and 50 µL of D.I water was added for samples. Next, 50 µL ASNase@HSN stock solution was added into the mixture, which was incubated at 37° C. for 50 min. After that, a 50 µL incubated sample was taken to mix with 100 µL Nessler's reagent, an extra 2.5 µL TCA was added for the test sample to quench the reaction, and the mixture was stood at room temperature for 10 min. Finally, the 100 µL sample was measured by absorbance at 480 nm for activity determination.

Catalase@HSN quantification: Catalase activity was determined by $H_2O_2$ assay. About 40 µg CAT@HSN was dispersed in 50 µL D.I water and mixed with 50 µL of 25 µM $H_2O_2$. They were incubated at 37° C. for 12 min in the dark for reaction. After that, the mixture was centrifuged to collect the supernatant and mixed with 100 µL diluted AmplexRed® reagent (A22188, Invitrogen) composed of 5 µL AmplexRed reagent, 10 µL 10 unit/mL HRP and 485 µL 50 mM phosphate buffer (pH=7.4) at room temperature for 10 min to detect the remaining $H_2O_2$. Then the sample was measured by fluorescence emission at 585 nm following excitation at 530 nm. The Catalase@HSN activity was estimated with a standard curve according to known concentration of $H_2O_2$.

Horseradish peroxidase(HRP)@HSN quantification: HRP activity was determined by a peroxidase assay. 50 µL HRP@HSN was mixed with 700 µL sodium phosphate buffer (SPB) (0.05M, pH=7.8) and 750 µL o-phenylenediamine dihydrochloride (OPD) solution (20 mg OPD in 50 mL SPB with 167 µL $H_2O_2$, pH=7.8) at room temperature for 1 h. Then, a 100 µL sample was well mixed with 1M phosphoric acid to stop the reaction and the mixture solution was measured by absorbance at 490 nm for activity determination.

Protein@HSN quantification by fluorescence correlation spectroscopy (FCS): the encapsulated protein number in HSN was also determined by FCS through a confocal laser scanning microscope (PicoQuant Microtime 200) with a 543 nm green laser. The fluorescence dye conjugated protein was used for protein@HSN synthesis and subsequent detection. The sample solution in 100 μL volume was placed on a glass slide and then the fluorescence dye was excited by 543 nm laser, and the fluorescence count rate was detected through the photodiode. The measurement process could be divided into three stages. First, the focal volume of FCS laser was measured to be a factor in the fitting correlation function. Here, a free dye, R6G, with a known diffusion coefficient (average residence time in the confocal volume) was used to measure the count rate and then the focal volume of 543 nm laser was confirmed. Based on the above, the count rate of RITC was detected to know the photon number released from RITC when it was excited. Second, the count rate of RITC-conjugated protein was derived by measuring various concentrations of RITC-conjugated protein to determine the correlation between concentration and count rate. It should be a linear correlation. Finally, the RITC-protein@HSN was measured through 543 nm laser to obtain the count rate for estimating how much protein is encapsulated in HSN.

Protease Tolerance Assay

400 μL of $2 \times 10^{-3}$ mg/mL protease mixture was dissolved in 10 mM NaOAc and 5 mM CaOAc (pH=7.5). Then, the protein@HSN was dissolved in 1 mL $H_2O$ and mixed with the protease solution. After incubation for 30 min at 30° C., the reaction solution was taken for determining the amount of remaining protein in the solution by enzyme activity assay.

Determination of Antigen@HSN Induced IgG Antibody by ELISA

The antigen-specific antibody induced by antigen@HSN was detected by enzyme-linked immunosorbent assays (ELISA). 96-well plates were coated with 100 μL of 10 μg/mL antigen solution in 0.05M carbonate/bicarbonate buffer (pH=9.5) at 4° C. for 20 h. Next, the solution in wells was drained out, 300 μL, 0.1M PBS (pH=7.2) containing 0.1% bovine serum albumin (BSA) was added into wells and the 96-well plates were shacked on an orbital shaker at room temperature for 1.5 h to wash out the non-adsorbed antigen. After that, 100 μL of 1600-fold diluted mouse plasma in 0.05% tween-20 PBS was added into plates and incubated at room temperature for 1 h or at 4° C. overnight. After incubation, the wells was washed with PBS twice, and then 100 μL diluted secondary antibody was added (1:10000 [HRP conjugated-2' antibody] or 1:200 [fluorescence dye conjugated-$2^{nd}$ antibody]) and incubated at room temperature for 1 h. If fluorescence dye conjugated-$2^{nd}$ antibody was used for detection, the sample was measured by fluorescence emission at 660 nm with excitation at 560 nm. If HRP conjugated-$2^{nd}$ antibody was used for detection, the sample was mixed with 100 μL fresh substrate solution containing 20 mg OPD in 0.1M citrate buffer, pH=6.0 and 167 μL $H_2O_2$, and incubated at room temperature for 30 min, after which 100 μL 1M phosphoric acid was added to stop the reaction and a 100 μL sample was taken for measuring the absorbance by spectrophotometer at 490 nm.

Her2 4T1 Cell Line Construction

Her2 expressed 4T1 cell was constructed from luc_4T1 cell by lentiviral particle infection. The lentiviral vector CHL0042, which was resistant to zeocin and pcDNA3.1(+)_NheI-HER2-HindIII-with EcoRI-AmCyan-XhoI, was digested and ligated with lentiviral vector by restriction enzyme and ligase, and the product was named plenti-zeo-HER2. Virus packaging followed the standard calcium phosphate transfection protocol: 10 μg plenti-zeo-HER2 plasmid, 9 μg p-CMV-Δ8.91 plasmid and 2.5 μg vesicular stomatitis virus G protein (VSVG) plasmid were mixed with HEBS (HEPES, NaCl, Dextrose, KCl and $Na_2HPO_4$) containing 2.5M $CaCl_2$, incubated at room temperature for 20 min and added to prepared $2 \times 10^6$ HEK293T cell in 10 cm dish dropwise for lentiviral particle production. The medium was replaced with fresh medium after 20 h and the virus-containing supernatants were collected after transfection for 72 h. Next, virus solution was collected and added to the prepared target cell, luc-4T1, incubated for 48 h in the presence of 8 ng/mL polybrene to infect the target cell. Finally, the cell was incubated with 100 μg/mL zeocin for 14 days to select Her2-luc transfected 4T1 cell line. Her2 protein expression was confirmed by IFC staining with anti-Her2/ERBB2 (cat.10004-RP04, Sino Biological) as first antibody and Alex fluor 488 goat anti-mouse IgG as secondary antibody.

Her2 ECD Protein Expression

The extracellular domain of Her2 expression vector, pET24-hHER2 ECD op, was bought from Genescript and transformed into BL21 to produce Her2_ECD protein. The Her2_ECD protein overexpression was induced by 0.5 mM IPTG at 37° C. for 4 h in *E. coli* (BL21). After incubation, BL21 were collected by centrifuge. Next, the cell was sonicated in 10% glycerol PBS under 4° C. to break up the cell and the solution was centrifuged to collect the pellet, which was rich in the Her2_ECD protein inclusion body. To the pellet was added 1.5% sarcosine to dissolve the Her2_ECD protein to solution with shaking overnight under 4° C. and then the supernatant rich in protein was collected by centrifuge. The protein solution was filtrated and purified through His-tag column (HisTrap FF, GE) by FPLC (AKTA pure, GE) with 200 mM imidazole phosphate buffer (0.05M NaH2PO4, 0.3M NaCl, pH=8) under 4° C. Purified protein was characterized by SDS-PAGE and western blot with anti-Her2/ERBB2 antibody (10004-RP04, SinoBiological) and quantified by nanophotometer (N60, IMPLEN).

IFN-γ Expression in CD8+ T Cells Analytical Method

Female C57BL/6 mice (6-8 weeks) were immunized with the same amount of neoantigen(NeoAg) or NeoAg@HSN on day 1, day 8 and day 15. About 300 μL of peripheral blood was collected from vaccinated mice on different days. The peripheral blood mononuclear cells (PBMCs) were separated by Histopaque®-1083 and transferred into a 96-well plate in 200 μL T cell culture medium (RPMI 1640 supplemented with 10% FBS, 100 $UmL^{-1}$ penn/strep, 55 μM β-mercaptoethanol, 1×MEM non-essential amino acid solution, and 1 mM sodium pyruvate). To carry out peptide re-stimulation, PBMCs were treated with various antigen epitopes (20 μg/mL) for 2 h. Subsequently, cytokine secretion was stopped by adding GolgePlug to the culture solution, which was incubated for another 4 h. Cells were pelleted and stained with anti-CD16/CD32 for 10 min at room temperature, and then the cells were stained with anti-CD8-FITC or anti-CD4-FITC for 20 min at room temperature. Cells were washed and subsequently fixed using 50 μL 2% formaldehyde solution overnight. The next day, cells were washed and permeated in 50 μL 0.5% saponin for 15 min at room temperature and then cells were washed and stained with anti-IFNγ-APC for 20 min. Finally, stained cells were pelleted and re-suspended in 200 μL buffer and analyzed using flow cytometry (BD FACSCanto II).

Synthetic Example 1

Synthesis of Protein@HSN

Asparaginase (ASNase)@HSN synthesis: 20 mL decane as oil, 3.5 mL CO-520 as surfactant, 1.1 mL hexyl alcohol as co-surfactant, and 2 mg ASNase were dissolved in 700 μL 1.43 mg/mL NaF and 500 μL 10 mg/mL NaF. All of the above were mixed to generate the reverse microemulsion system. Then, a part of silica source, 50 μL 8-fold diluted APTMS by ethanol and 200 uL of TEOS, was added into the system, which was continuously stirred at 20° C. 1 h later, another part of silica source, 504, diluted APTMS and 200 μL of TEOS, was added into the system, which was continuously stirred at 20° C. for 20 h. After a night of stirring, 500 μL of ammonium hydroxide (aq) (2.24-2.4 wt %) was slowly introduced into the mixture with stirring for 20 min. Next, 50 μL TEOS was added into the mixture dropwise, which was stirred for 4 h, and then, 250 μL PEG-silane and 25 μL TEOS was added and stirred at 20° C. for 20 h to modify the particle surface. After that, 95% ethanol was added to destabilize the microemulsion system and particles were collected by centrifuge at 14,000 rpm for 20 min. The particles were washed with 95% ethanol once and D.I water twice, and transferred into 80 mL D.I water. Then, the solution was kept in 40° C. and stirred for 1 h to obtain the ASNase@HSN. Finally, the ASNase@HSN was collected by centrifugation, washed with D.I water twice, and stored in D.I water at 4° C.

Horseradish peroxidase (HRP)@HSN synthesis: The synthesis process of HRP@HSN was the same as described for ASNase@HSN, but the enzyme 2 mg ASNase was replaced with 2.67 mg HRP.

Catalase@HSN synthesis: 20 mL decane as oil, 3.5 mL CO-520 as surfactant, 1.1 mL hexyl alcohol as co-surfactant, and 50,000 unit catalase were dissolved in 1200 μL 10 mg/mL NaF. All of the above were mixed to generate the reverse microemulsion system. Then, a part of silica source, 50 μL 8-fold diluted APTMS by D.I water and 200 μL of TEOS, was added into the system, which was continuously stirred at 20° C. 2 h later, 250 μL 8.5 mM ammonium hydroxide (aq) was added and stirred for 20 min; then, another part of silica source, 50 μL diluted APTMS and 200 uL of TEOS was added into the system, which was stirred at 20° C. for 20 h. After stirring was done for a night, 100 μL of ammonium hydroxide (aq) (5.6-6 wt %) was slowly introduced into the mixture with stirring for 10 min. Next, 50 μL TEOS was added into the mixture dropwise and stirred for 2 h, and then, 250 μL PEG-silane and 25 μL TEOS were added and stirred at 20° C. for 20 h to modify the particle surface. After that, 95% ethanol was added to destabilize the microemulsion system and particles were collected by centrifuge at 14,000 rpm for 20 min. The particles were washed with 95% ethanol once and D.I water twice, and transferred into 80 mL D.I water. Then, the solution was kept at 40° C. and stirred for 1 h to obtain the catalase@HSN. Finally, the catalase@HSN was collected by centrifugation, washed with D.I water twice, and stored in D.I water at 4° C.

TEM and DLS Measurements

The protein@HSN nanoparticles as synthesized in Example 1 were subjected to TEM measurements and the results suggest that all the protein@HSNs had an average particle size of around 50 to 95 nm and small standard deviations of particle size, which reflect the uniformity of the particles. The particle size of the protein@HSNs was measured via Dynamics Light Scattering (DLS) in different solution environments. The DLS results show that protein@HSNs dispersed well within the range from about 60 to about 100 nm in water, PBS and serum containing medium.

Quantification of Protein@HSN

The amount of protein encapsulated in the silica nanoparticles was about 1%-7% (weight percent). The quantification results are derived from enzyme activity or fluorescence correlation spectroscopy, with the methodology described above.

Protease Tolerance Assay

To determine the protective effect of the HSN disclosed herein on the ASNase encapsulated therein from protease degradation, free ASNases or ASNases encapsulated in HSN (NTT3_39) were subjected to protease digestion, and the remaining ASNase activity was determined by ASNase activity assay. Hence, protease tolerance tests were performed to evaluate the protective effect of the HSN on the ASNases encapsulated therein.

Figure 2:
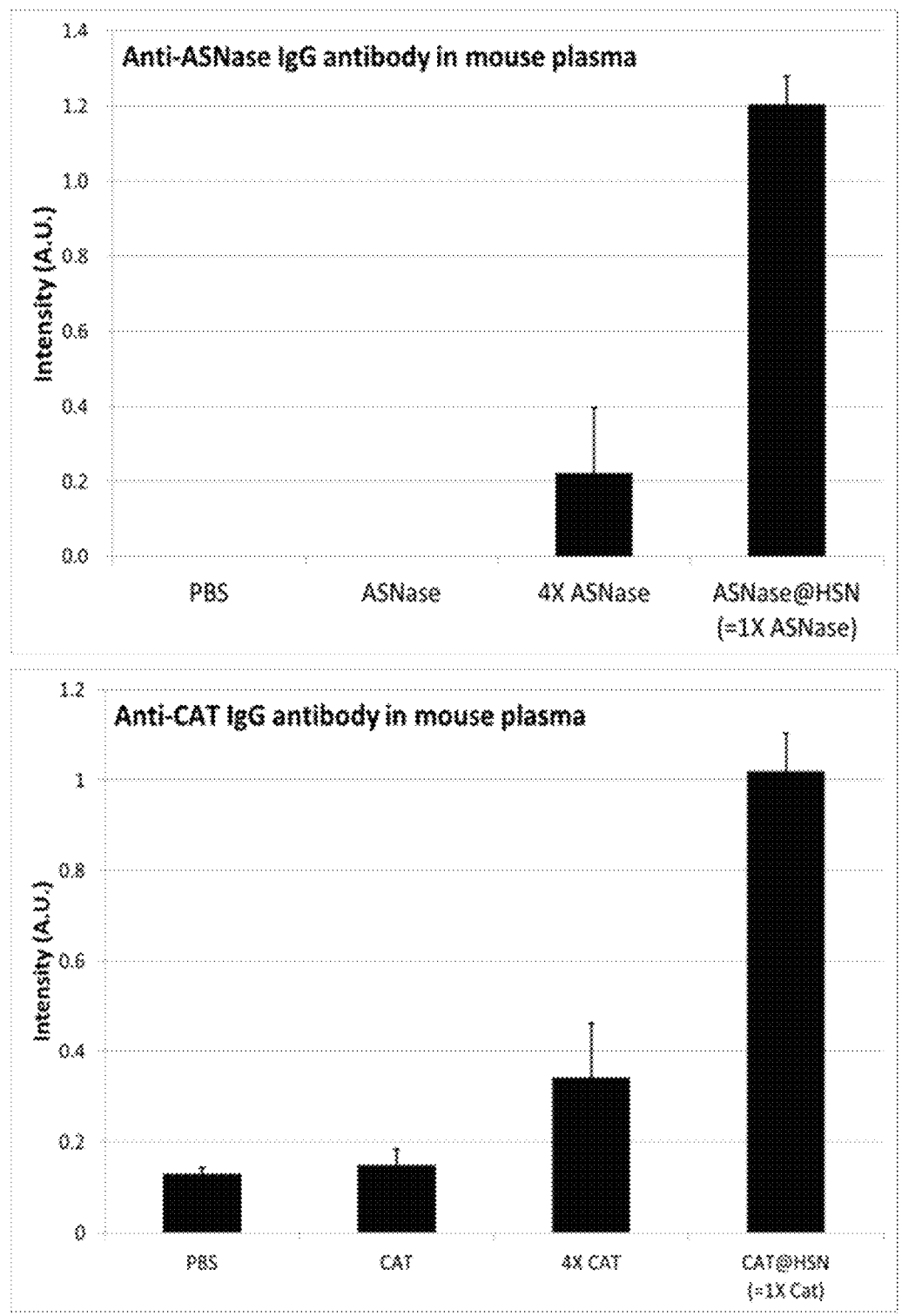
FIG. 2 shows the effects of antigen(protein)@HSN inducing antigen specific antibody in mouse.
Figure 2:
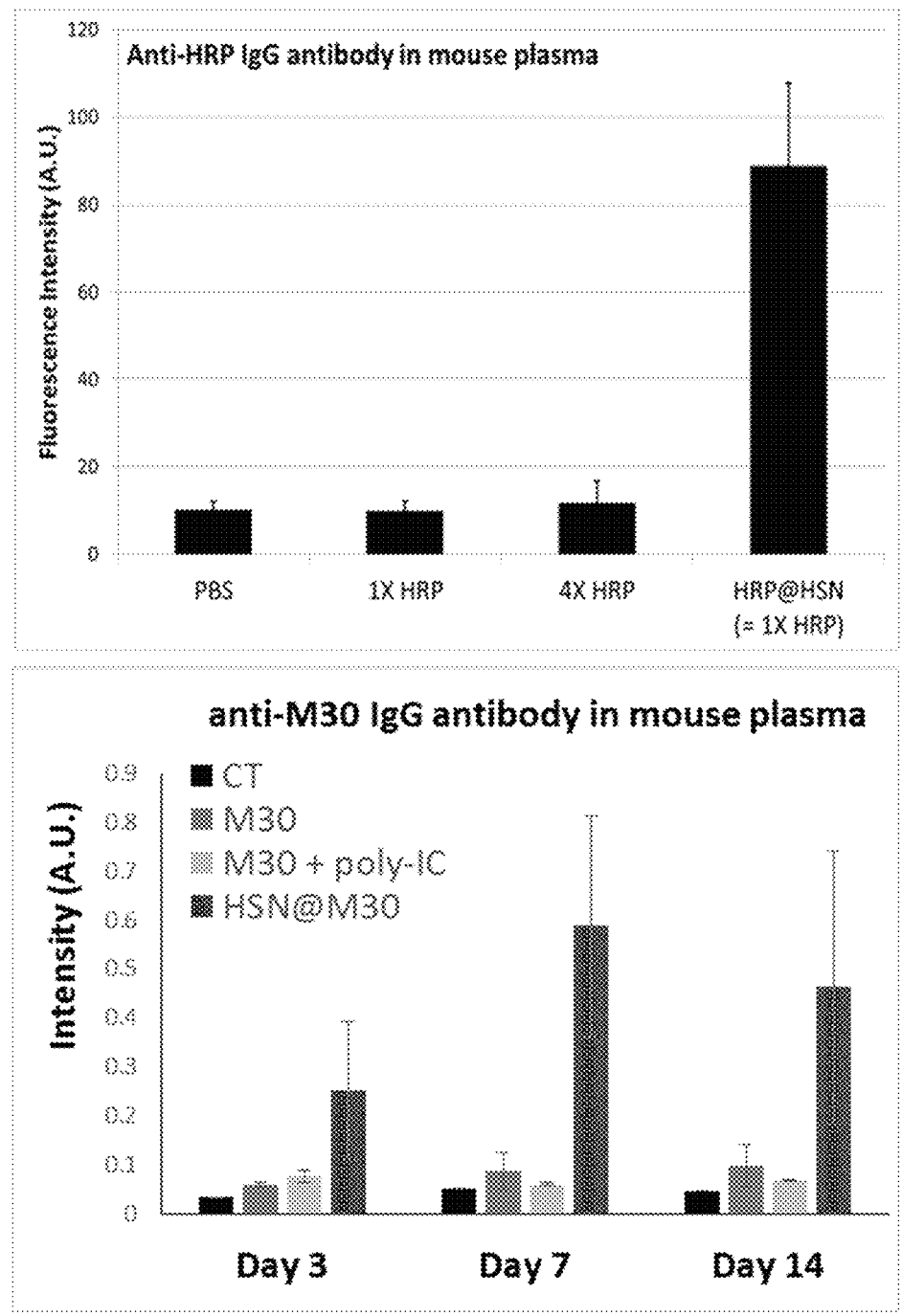

Free ASNases and ASNases encapsulated in HSN (NTT3_39), all containing the same amount of ASNases, were centrifuged and dispersed in 1 mL of PBS buffer (pH 7.5), mixed with 400 uL protease solution ($2 \times 10-3$ mg protease/mL in 10 mM NaOAc+5 mM CaOAc (pH 7.5)), and subjected to protease digestion at 37° C. for 30 mins. After digestion, the ASNase activity in the samples was determined by ASNase activity assay. It can be clearly observed that, after degradation with a protease mixture for 30 minutes, the activity of free ASNase was decreased to less than 20% of original activity. However, NTT3_39, which encapsulated ASNase, exhibited excellent protective effect. The results revealed that once the protein (antigen) is suspended in solution, it will be degraded quickly by the protease. Hence, if the protein is attached to nanoparticles through a non-covalent bond, once the particle is injected into the body, the protein will start to leak from the particle, leading to degradation. Encapsulated antigens inside the HSN are able to provide excellent protease protection.

HSN Lymph Node Targeting

The efficiency of inducing adaptive immunity largely depends on the proper targeting of the immune system, especially the lymph nodes. The lymph node is the site where antigen-specific T cells are activated and primed. Using nanoparticles to deliver antigen directly to lymph nodes would improve both the efficacy and safety of antigen-specific immune response. For developing HSN with lymph node targeting ability, the size and suspension in solution of HSN is important. A near-infrared fluorescence-emitting dye (cy5.5) conjugated HSN about 50-100 nm in size (detected by TEM) and monodispersion in water and buffer solution was subcutaneously injected in the hind footpads of mice and the biodistribution of HSN was detected at different time points by IVIS to explore the lymph node targeting ability of HSN. Cy5.5-HSN was first focused at the injection site and persisted in lymph nodes up to 7 days. At day 7 after administration, mice were dissected and there were significant fluorescence signals at inguinal LN, popliteal LN, iliac LN and renal LN (FIG. 1). This result reveals that the smaller size and good suspension of HSN exhibit lymph node targeting ability which, is an advantage for an antigen delivery vehicle for vaccine.

Protein@HSN Induce Immune Response

Asparaginase encapsulated HSN (ASNase@HSN) of smaller size (about 65 nm) and good suspension in solution was used to test the antigen-specific immune response. The mice were intravenously, subcutaneously or intramuscularly injected individually with 20 μg of ASNase or ASNase@HSN with the same protein amount in 200 μL PBS once a week for three weeks; 75-100 μL blood was harvested at day 17 and the ASNase-specific antibody level of serum was detected by ELISA assays. The serum of ASNase immunized mice did not show the ASNase-specific antibody signal. Even though the ASNase dose was quadrupled, just a few antibodies were detected. In contrast, ASNase@HSN induces a significant amount of ASNase-specific antibody as compared with ASNase (FIG. 2). The different ASNase@HSN administration routes exhibit a similar level of ASNase-specific antibody induction. Furthermore, replacing the ASNase with other proteins such as catalase and horseradish peroxidase as antigen still exhibits a strong immune response as compared with the antigen only group. Therefore, antigen encapsulated by HSN significantly enhances the immunogenicity of the antigen and allows various administration routes.

Her2 4T1 @HSN and HSN Immunotherapy

Figure 3:
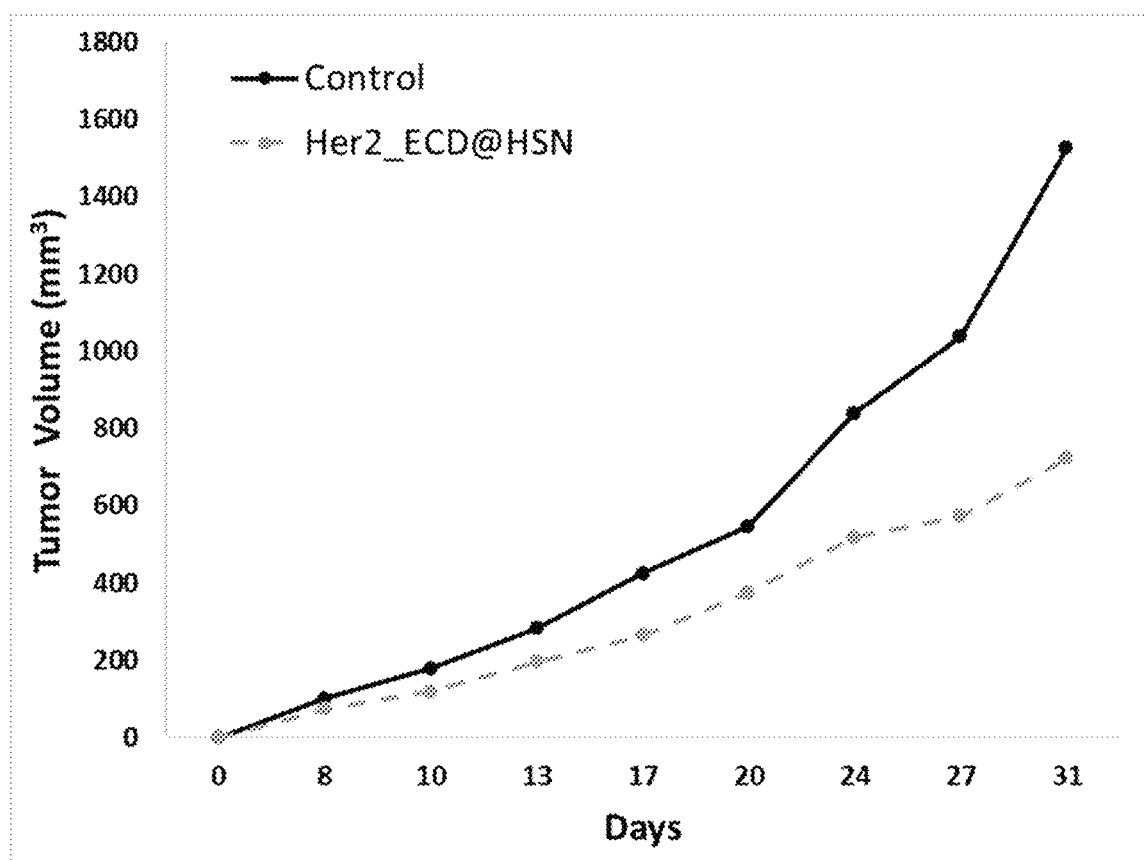
FIG. 3 shows the Her2_ECD @HSN in immunotherapy anti-tumor efficacy.

To demonstrate the potential of antigen@HSN as cancer vaccine, Her2 extracellular domain protein was chosen as the antigen and encapsulated into HSN. To prove Her2_ECD@HSN can induce immune response and repress the Her2 associated cancer proliferation, the animal model was constructed by implanting the Her2 overexpressing breast cancer cells subcutaneously (s.c.) into the flank of immunocompetent BALB/c mice. The Her2 overexpressing breast cancer cell line (Her2_4T1) was generated by transduction of breast cancer cell line 4T1 with retroviral vector encoding the cDNA for human Her2. BALB/c mice were intravenously vaccinated with Her2_ECD@HSN three times at one-week interval. One day after the third vaccination, Her2_4T1 cells were implanted subcutaneously into the flank of the mice, and the tumor size was monitored twice a week. The mice vaccinated with Her2_ECD@HSN revealed significant inhibition of tumor growth compared to control group (FIG. 3), and the amount of anti-Her2_ECD antibody in the plasma was also higher than control group. This result represents that Her2_ECD@HSN can successfully induce Her2 specific adaptive immune response to repress tumor proliferation. This verifies that antigens encapsulated by HSN can enhance the immunogenicity and immunotherapy efficacy.

Figure 4:
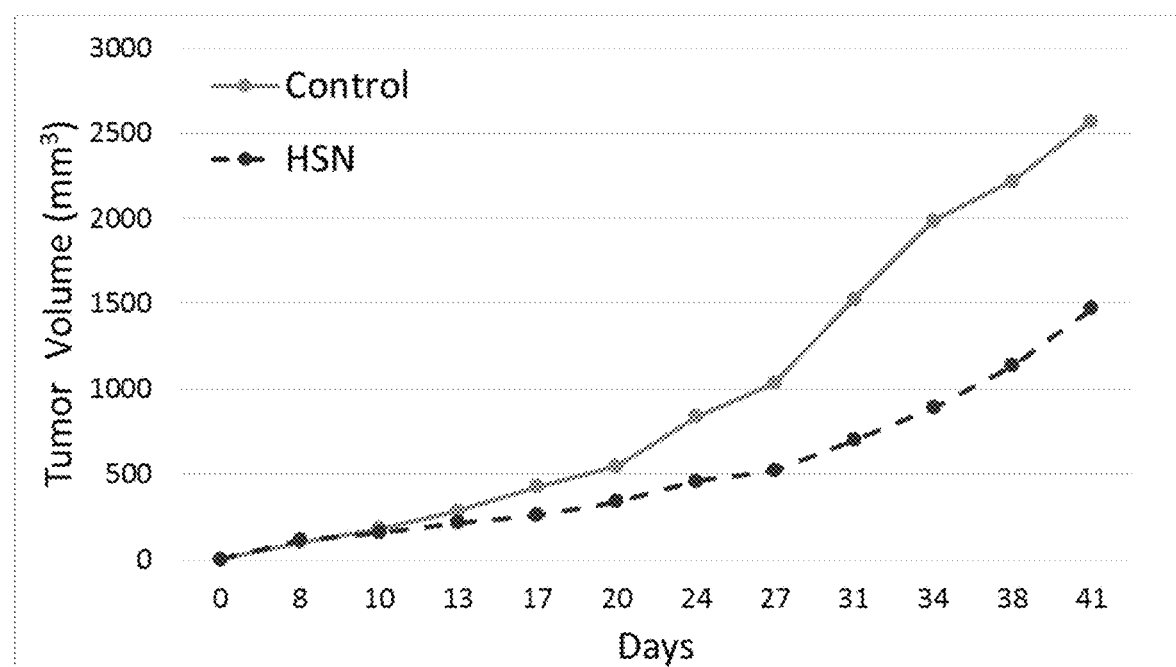
FIG. 4 shows the anti-tumor efficacy of HSNs.

According to the immunotherapy results mentioned above, antigen@HSN can enhance the immune response significantly because HSN can be a carrier and self-adjuvant at the same time. The smaller size and good suspension of HSN in this invention bestows properties such as lymph node targeting, tumor targeting (EPR effect), and self-immunogenicity (self-adjuvant). These properties allow HSN to potentially be employed in another treatment method for anti-tumor growth, wherein the HSN particle (without antigen encapsulation) is administered intravenously into the body; the particles are able to accumulate in the lymph node and tumor. After that, the HSN will induce immune response locally and modulate the tumor microenvironment simultaneously because the HSN with self-adjuvant property accumulated in tumor. The enhancing immune response may trigger the antitumor immunity to repress tumor growth. To demonstrate the concept, mice were implanted with Her2_4T1 cells on the flank subcutaneously and treated with HSN through intravenous administration at day 3, 10, 17 after tumor implantation. The mice treated with HSN showed smaller tumor size compared to control group. We also tested the anti-tumor efficacy of HSN in 4T1 tumor animal model, which revealed that HSN can inhibit 4T1 tumor growth (FIG. 4). In contrast, according to our previous experiments, tumor growth was not inhibited in the mice treated with MSN only (without drugs). These results represent that HSN has some special and unique properties different from other silica nanoparticles, making HSN exhibit higher immunogenicity and immunotherapeutic efficacy.

HSN Induce Locally Immune Response in Tumor

Figure 5:
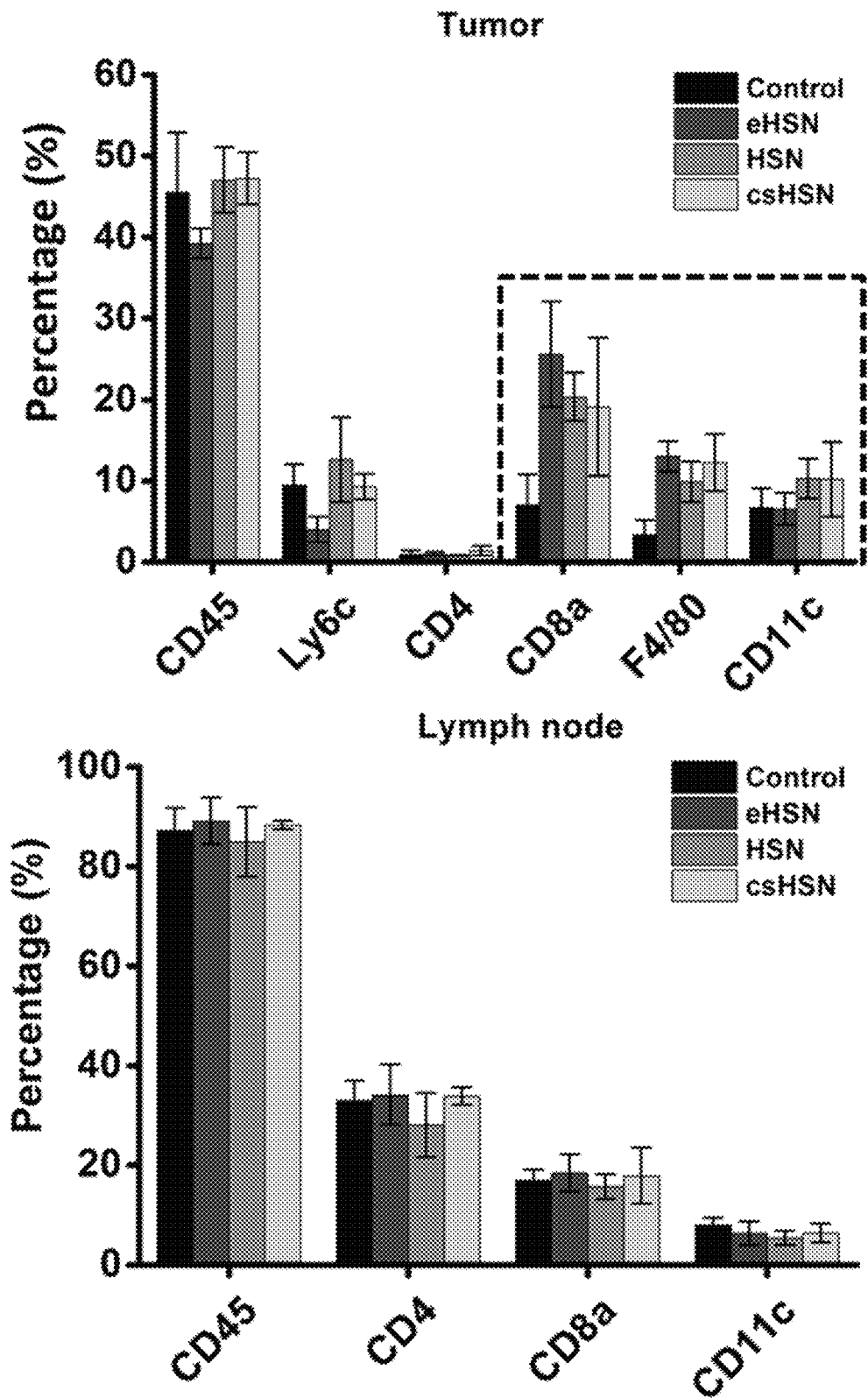
FIG. 5 shows CD8 T cell, dendritic cell, and macrophage which are locally increased in tumor due to the presence of HSNs without systemic immune response.
Figure 5:
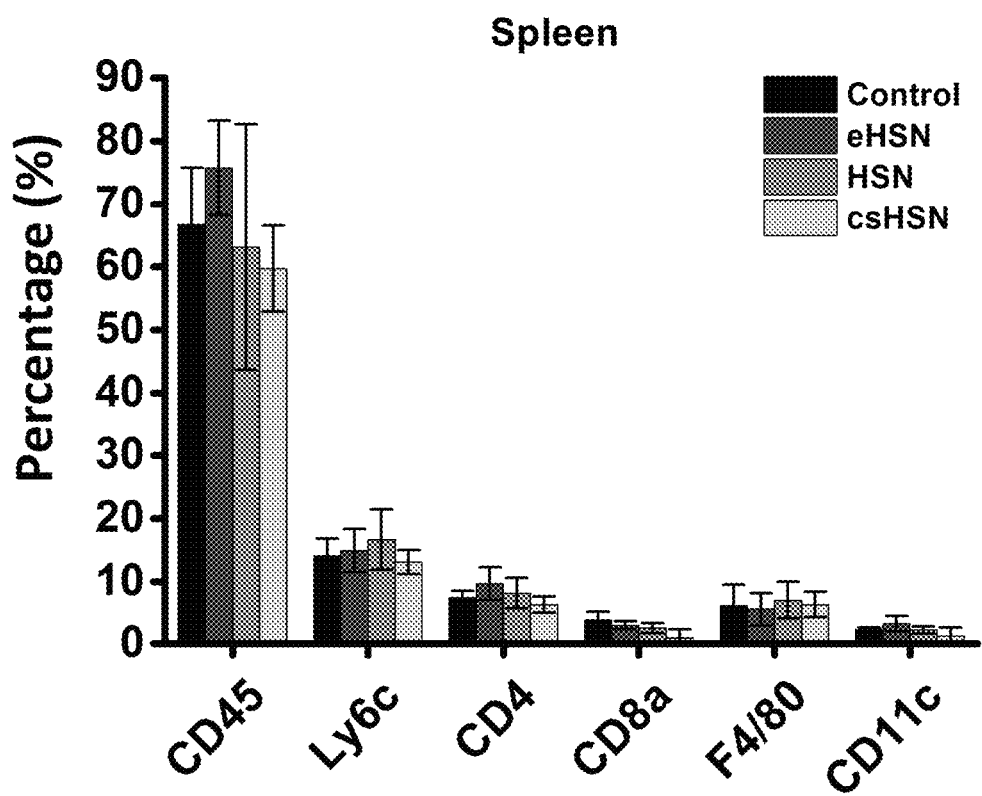

The 4T1-tumor bearing mice vaccinated with different kinds of HSNs three times at one-week internal, one day after last vaccination, spleen, lymph nodes and tumor were collected and digested for subsequent immune cell staining. The immunophenotyping in spleen and lymph nodes of the mice vaccinated with HSNs is similar with control group mice, in contra, the populations of CD8a$^+$, F4/80 and CD11c cells in tumor are increased, it mean that the cytotoxic T cells, macrophage, and dendritic cells are recruited around tumor (FIG. 5). These results demonstrated that the smaller size and good suspension of HSN can accumulate in tumor through EPR effect and recruit immune cells around tumor lead to the enhancement of tumor-infiltrating immune cells in the tumor site and inhibition of tumor growth without systemic adverse effect.

Neoantigen@HSN Synthesis and Methods of Improving Loading Capacity of Peptide Encapsulated Silica Nanoparticle Neoantigen is a class of HLA-bound peptides that arise from tumor-specific mutations. They can be used as biomarkers differentiating cancer cells from normal cells. Hence the neoantigen peptide is a good antigen for developing antigen@HSN for cancer immunotherapy. The NeoAg@HSN was synthesized by the method of protein@HSN synthesis mentioned above, and the protein was replaced with neoantigen peptide. However, it was unexpectedly found that the peptide could not be efficiently encapsulated in HSN. At the process of microemulsion destabilization, most neoantigen peptides are suspended in the supernatant and barely detected in the HSN. This unexpected result may be due to the fact that a peptide is usually composed of hydrophobic and hydrophilic amino residues; the amphiphilic property of peptides may leads to a strong interaction between peptide and poly(ethylene glycols)-containing surfactant such as IGEPAL® CO520, Triton X-100 and tween 20. These kinds of non-ionic surfactants are commonly used in reverse microemulsion systems. To solve this problem, three methods were proposed for enhancing peptide loading capacity of silica nanoparticles: (1) the poly(ethylene glycols)-containing surfactant used in reverse microemulsion was replaced with a surfactant which is absent of oxyalkylene units or a surfactant which is ionic surfactant such as dioctyl sulfosuccinate sodium salt (AOT), cetyltrimethylammonium bromide (CTAB); (2) the peptide was designed to decrease the amphiphilic property of peptide and increase the interaction between peptide and silica molecule, to make the peptide more easily surrounded by silica molecules and easily caged in the silica nanoparticle. The peptide was designed via adding a polycharged motif before, after, or to both sides of the peptide sequence and inserting an enzyme-cleavable sequence between the polycharged motif and peptide sequence; (3) a molecule or particle which had affinity toward neoantigen peptide was added into water phase of microemulsion to increase the peptide encapsulation efficiency such as 1. electrostatic interaction between positively charged neoantigen and negatively charged molecule; 2. Van der Waals interaction between hydrophobic neoantigen and less charged or non-charged molecule; 3. A cleavable covalent bond including disulfide bond, enzyme-cleavable sequence, acid-cleavable moieties between neoantigen and molecule. The molecule and neoantigen can be individual or pre-mixed before adding into the water phase of microemulsion. The molecule can be silane, polymer, dendrimer, or silica nanoparticle. The NeoAg@HSN can be successfully synthesized by using the designed neoantigen peptide (in one embodiment, adding a polyarginine sequence and an enzyme-cleavable sequence at N-terminal of original neoantigen peptide. In on embodiment, adding a thiol group amino acid at N-terminal of original neoantigen peptide) and the amount of peptide in NeoAg@HSN is detectable.

Synthesis of Positive Charge Moieties Modified Neoantigen@HSN

Synthesis process: mix 20 mL decane, 3.5 mL CO-520 and 1.1 mL hexyl alcohol, then added the water phase solution of 1-2 mg positive charge moieties modified neoantigen dissolved in 350 μL D.I water, 250 μL 10 mg/mL NaF and 25 μL diluted APTMS into oil phase with stirring for 30 min to generate the microemulsion system, then 100 μL TEOS was added into the system and stirred for 1 h. After, 25 μL diluted APTMS and 100 μL TEOS were added and stirred at 20° C. for 18 h. On the second day, 500 μL 28-30 wt % $NH_{3(aq)}$ and 100 μL TEOS were added and stirred at 20° C. for 4 h, then, 250 μL PEG-silane, 25 μL TEOS were added and stirred at 20° C. for 16-18 h. On the third day, the particle was collected by adding 2-fold volume of 95% ethanol to destabilize the microemulsion system and centrifuge at 14000 rpm for 20 min. The particle was washed by 95% ethanol twice and D.I water once, and transferred into 80 mL D.I water. Then, the solution was kept in 40° C. and stirred for 1 h to remove the superfluous residue. Finally, the neoantigen@HSN were collected by centrifugation and washed by D.I water twice. The loading amount of neoantigen in neoantigen@HSN is higher than 1% weight percent and the particle size measured via TEM and DLS is shown in Table 1.

TABLE 1

| Neoantigen sequence | Size of NeoAg@HSN | |
|---|---|---|
| | TEM size (nm) | DLS size in PBS (nm) |
| MC38-mS: RRRRGFLGASMTNMELM | 82.6 ± 4.5 | 126.1 |
| MC38-mL: RRRRRRGFLGGIPVHLELASMT NMELMSSIVHQQVFPT | 52.8 ± 3.5 | 81.0 |

Synthesis of Thiol Moieties Modified Antigen@HSN

There are two steps in the synethesis process 1. thiol moieties modified antigen mix with a orthopyridyl disulfide (OPSS)-containing silica nanoparticle to generate disulfide bond between antigen and silica particle 2. Introducing the Ag-silica nanoparticle solution as a water phase into a microemulsion system to synthesize the antigen@HSN.

1. Mixture of Antigen and OPSS-Silica Nanoparticle 50 mg OPSS-silica nanoparticle were dispersed in 6.3-7 mL DI water, and then added 375 uL acetate buffer (100 mM, pH4.2) acidic buffer or 375 uL $NaH_2PO4$ (100 mM, pH6.5) and 750 uL NaOH (25 mM) alkaline buffer into the solution. Stir solution until homogeneous, and add 75-150 uL antigen solution (10-20 mg/mL). Keep stirring for 1-3 days at 4° C. or room temperature. After that, wash the particle with 20% ACN/DMSO with 0.025%TFA and water. Centrifuge the solution to get the particle and the supernatant was analyzed for determining the antigen loading amount by HPLC.

2. Synthesis of Thiol Moieties Modified Antigen@HSN 37.5 mL Decane, 6.56 mL Igepal CO-520, and 2.06 mL hexanol mixed together, and stirred at 20° C. Add 2250 uL antigen-silica nanoparticle (50 mg/2250 uL) as water phase into the mixture, and then stir at 20° C. for 10 minutes. Introduce 37.6 uL 8-fold diluted APTMS, 150 uL TEOS and 83.34 uL 28% NH4OH into the mixture, stir at 20° C. for 10 minutes. After that, add 37.6 uL 8-fold diluted APTMS, 150 uL TEOS and 83.34 uL 28% NH4OH into the mixture, stir at 20° C. for 4 hours. Then, add 37.6 uL TEOS and 375.2 uL PEG-silane into the mixture and stir at 20° C. overnight. 20 mL ethanol was introduced into the solution to destroy the microemulsion system and centrifuged at 14000 rpm for 15 min to get the antigen@HSN particle. Wash the particle with ethanol and water twice and store in water. The particle size (TEM) is less than 100 nm and the hydrodynamic diameter of particles measured via DLS in PBS is less than 150 nm.

NeoAg@HSN Immunogenicity (IFN-γ Expression in CD8+ T Cells) and Immunotherapy

Figure 6:
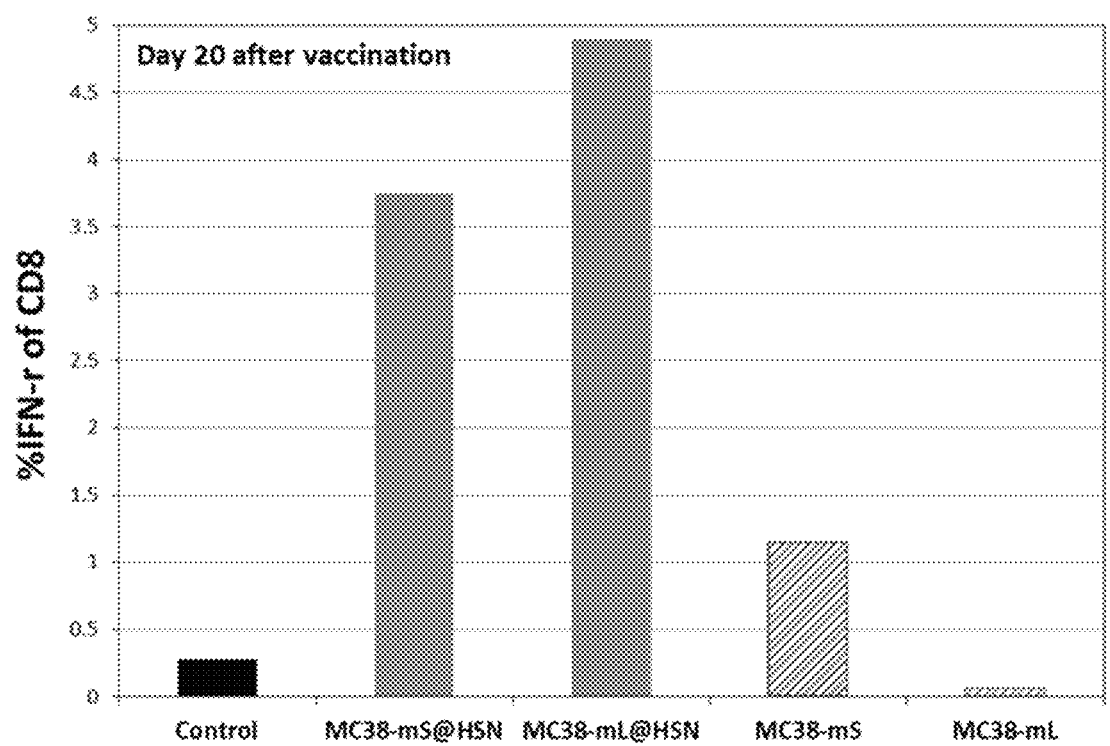
FIG. 6 shows the results of IFN-r expression in CD8 T cell on day 20 after vaccination by NeoAg@HSN.

Female C57BL/6 mice (6-8 weeks) were immunized with NeoAg solution (containing 50 ug MC38_mS or MC38_mL neoantigen peptide with or without 50 ug poly-IC) and NeoAg@HSN solution (MC38_mS@HSN or MC38 mL@HSN solution which contained 50 μg neoantigen peptide with or without 50 ug poly-IC) individually on day 1, day 8 and day 15. About 300 μL of peripheral blood was collected from vaccinated mice on day 28 and day 35. The method of detecting IFN-r expression in CD8 T cells was described above. The mice immunized with MC38_mS@HSN or MC38_mL@HSN showed significantly higher IFN-r expression in CD 8 T cell compared to the mice immunized with MC38_mS or MC38_mL peptide (FIG. 6). This result shows that the HSN can be a carrier and self-adjuvant to enhance the immunogenicity of neoantigen peptide. The immunotherapy results revealed that the mice immunized with NeoAg@HSNs three times at one-week interval had repressed MC38 tumor growth, while the tumor size of the mice immunized with NeoAg peptides+poly-IC (adjuvant) was similar to the control group.

We claim:

1. A method for inhibiting tumor growth in a subject in need thereof, consists administration of hollow silica nanospheres (HSNs) to the subject, wherein the HSNs increase tumor-infiltrating immune cells in a tumor, wherein the HSNs comprise a single or multi-layered silica shells, wherein each shell has meso-pores and encloses a closed hollow space, optionally the innermost hollow closed space has a solid silica core, wherein the space is defined by the distance between any two silica shells or the solid silica core, and wherein the hydrodynamic size of HSNs in a medium measured via Dynamics Light Scattering (DLS) is no greater than 150 nm, wherein the medium is biologically similar to or equivalent to phosphate buffered saline (PBS), wherein the HSNs are administered to the subject either (i) unloaded such that the HSNs act as a self-adjuvant to increase tumor-infiltrating immune cells in the tumor, or (ii) loaded with a bioactive ingredient such that the HSNs act both as a carrier and self-adjuvant to increase tumor-infiltrating immune cells in the tumor.

2. The method of claim 1, wherein the hydrodynamic size of HSNs is no greater than 100 nm.

3. The method of claim 1, wherein the administration route of HSNs can be systemic administration or local administration.

4. The method of claim 3, wherein the systemic administration is intravenous injection or infusion.

5. The method of claim 1, wherein the HSNs are loaded with the bioactive ingredient and act both as a carrier and self-adjuvant.

6. The method of claim 5, wherein the bioactive ingredient is a neoantigen.

7. The method of claim 6, wherein the neoantigen is a tumor-specific neoantigen.

8. The method of claim 6, wherein the neoantigen is a tumor-specific neoantigen, a tumor neo-epitope, a tumor-specific neoantigen, a tumor neo-epitope, a neoantigenic peptide, a neoantigenic DNA, or a neoantigenic RNA.

9. The method of claim 6, wherein the neoantigen is a peptide having no more than 200 amino acids.

10. The method of claim 6, wherein the neoantigen is a DNA or RNA molecule having no more than 1200 nucleobases.

11. The method of claim 5, wherein the bioactive ingredient is selected from the group consisting of an enzyme, a protein drug, an antibody, a vaccine, an antigen, an antibiotic and a nucleotide drug.

12. The method of claim 1, wherein the tumor-infiltrating immune cells are cytotoxic T cells, macrophage or dendritic cells.

13. The method of claim 1, wherein the tumor-infiltrating immune cells are T cells, B cells, natural killer cells, neutrophils, mast cells, eosinophils or basophils.

14. The method of claim 1, wherein the HSNs are administered unloaded such that the HSNs act as a self-adjuvant to increase tumor-infiltrating immune cells in the tumor.

* * * * *